United States Patent [19]

Kapsokavathis et al.

[11] Patent Number: 5,103,184
[45] Date of Patent: Apr. 7, 1992

[54] CAPACITIVE FUEL COMPOSITION SENSOR WITH GROUND ISOLATION

[75] Inventors: Nick S. Kapsokavathis, Rochester; Stephen P. Sanders, Flint, both of Mich.

[73] Assignee: General Motors Corporation, Detroit, Mich.

[21] Appl. No.: 615,693

[22] Filed: Nov. 16, 1990

[51] Int. Cl.⁵ .............................. G01R 27/26
[52] U.S. Cl. ........................ 324/672; 324/663; 324/608; 73/61.1 R
[58] Field of Search ............... 324/663, 603, 690, 605, 324/609, 664, 679, 688, 690, 665, 608; 73/61.1 R; 364/424.01, 431.03, 431.05, 481

[56] References Cited

U.S. PATENT DOCUMENTS

| | | | |
|---|---|---|---|
| 2,720,624 | 10/1955 | Gunst et al. | 324/61 |
| 3,768,006 | 10/1973 | Mueller | 324/665 |
| 3,816,811 | 6/1974 | Cmelik | 324/61 R |
| 4,001,676 | 1/1977 | Hile et al. | 324/60 CD |
| 4,470,300 | 9/1984 | Kobayashi | 73/304 |
| 4,915,084 | 4/1990 | Gonze | 123/575 |
| 4,939,467 | 7/1990 | Noglami et al. | 324/663 |
| 4,939,468 | 7/1990 | Takeuchi | 324/690 |
| 4,971,015 | 11/1990 | Gonze | 123/494 |

FOREIGN PATENT DOCUMENTS 1232675 5/1971 United Kingdom .

OTHER PUBLICATIONS

SAE Paper 900231, "Intelligent Alcohol Fuel Sensor", 2/90, esp pp. 3-7.
IEE Transactions on Vehicular Technology, vol. VT-27, No. #, Aug./78, "An On-Board Sensor for Percent Alcohol", pp. 142-144.

*Primary Examiner*—Jack B. Harvey
*Attorney, Agent, or Firm*—Robert M. Sigler

[57] ABSTRACT

A fuel composition sensor for a fuel line carrying a mixture of two fuels provides a fuel composition signal VOUT to an engine control computer having a computer analog reference voltage ECM referenced to a computer ground EGD. The sensor has a sensor analog reference voltage VREF referenced to a sensor ground GND, which may differ from the computer ground EGD. An input isolation amplifier derives the sensor analog reference voltage VREF relative to GND ratiometrically from the computer analog reference voltage ECM referenced to EGD; and an output isolation amplifier derives the fuel composition signal VOUT referenced to EGD ratiometrically from the difference between a fuel composition responsive sensor signal VSIG and its minimum possible value, corresponding to a sensed fuel composition of only one of the fuels, relative to GND. The sensor may comprise a capacitive voltage divider and provide sensor voltage VSIG also having a maximum value corresponding to a sensed fuel composition of only the other fuel. If the range of possible values of VSIG is compressed, the isolation amplifier may provide a gain greater than one to better match the available input range of the computer. The minimum value of the fuel composition signal may be set detectably greater than EGD so that a value of EGD signals a sensor fault.

10 Claims, 5 Drawing Sheets

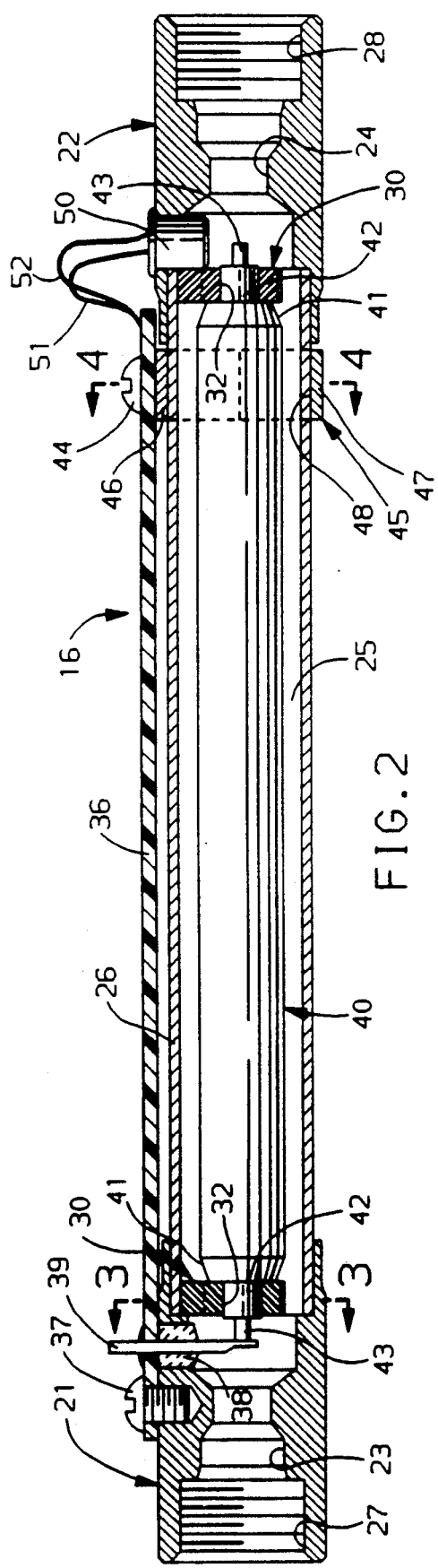
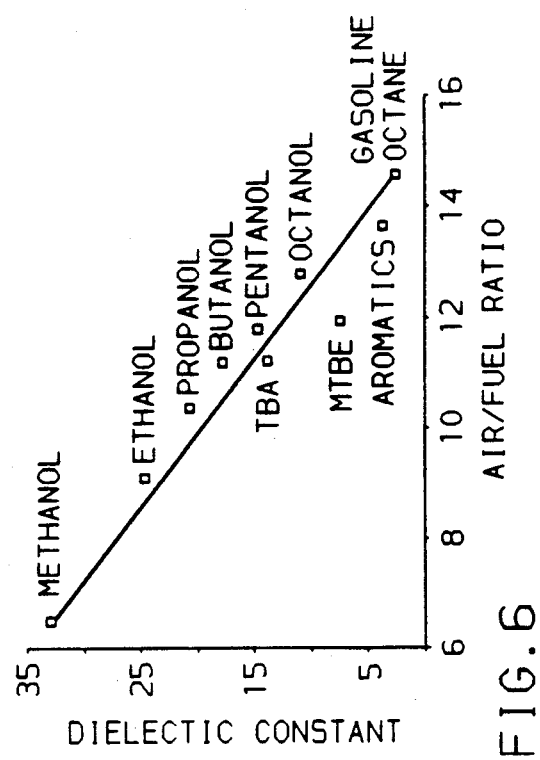
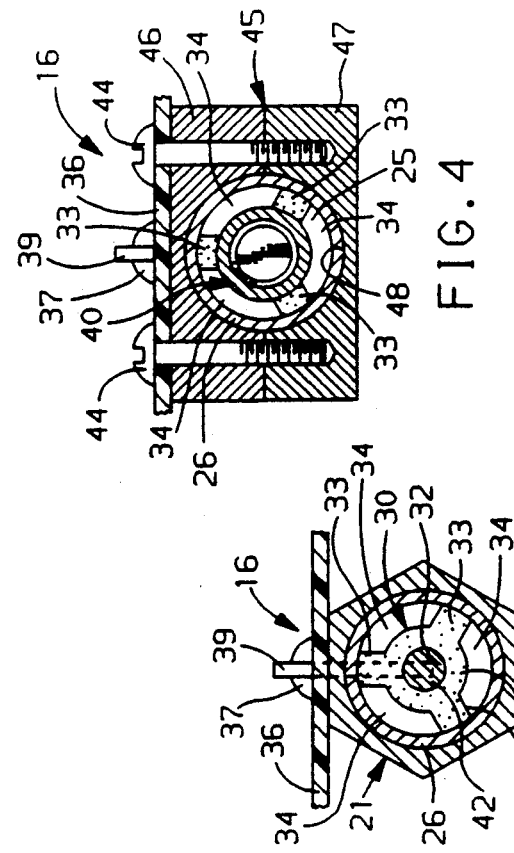

CAPACITIVE FUEL COMPOSITION SENSOR WITH GROUND ISOLATION

BACKGROUND OF THE INVENTION

This invention relates to combustion engine driven vehicles and particularly to such vehicles adapted to operate on a mixture of fuels such as gasoline and alcohol in unknown, variable concentrations. The engines of such vehicles are optimally operated with one or more engine operating parameters varied in response to a fuel composition signal generated by a sensor in the engine fuel supply which is responsive to a parameter of the fuel mixture indicating fuel composition.

The fuel composition signal is preferably provided to an engine control computer programmed so as to control the fuel composition affected engine operating parameters in response to the signal. Such an engine control computer is powered from a vehicle electrical power supply which provides a computer analog reference voltage relative to a computer ground voltage. To be most accurate and meaningful, the voltage of the fuel composition signal input to the computer should be referenced to the computer ground voltage and should have a range between its maximum and minimum possible values which is optimally matched to the allowable input voltage range of the computer.

However, the cost of the fuel composition sensor may be significantly reduced if one of the capacitor electrodes is grounded, since that electrode need not be insulated from the vehicle body. If this is done, the sensor ground voltage may differ from the computer ground voltage by as much as a volt. In addition, the sensor has its own power supply providing its own analog reference voltage; and the sensor output voltage may further be compressed or expanded relative to the range of allowable input to the computer. Thus, the sensor output voltage is not necessarily optimally matched to the input of the engine control computer.

SUMMARY OF THE INVENTION

It is therefore an object of this invention to provide a fuel composition sensor apparatus for a fuel mixture of two fuels to provide a fuel composition signal for input to an engine control computer which is referenced to the computer ground voltage and varies within a range optimally matched to the allowable input voltage range of the computer.

The apparatus provides for this purpose an input isolation amplifier for deriving a sensor analog reference voltage VREF, referenced to the sensor ground voltage GND, ratiometrically from the computer analog reference voltage ECM, referenced to the computer ground voltage EGD. The apparatus further provides an output isolation amplifier for deriving the fuel composition signal VOUT, referenced to the computer ground voltage EGD, ratiometrically from the difference between the sensor voltage VSIG and a minimum value thereof, corresponding to a sensed fuel composition of only one of the fuels, referenced to the sensor ground voltage GND.

The sensor may be of the capacitive type with a voltage divider comprising a sensor capacitor in series with a reference capacitor for determining a proportion of the sensor analog reference voltage VREF relative to the sensor ground voltage GND indicative of fuel composition for derivation of the sensor voltage VSIG. The sensor output voltage may further have a maximum possible value corresponding to a sensed fuel composition of only the other of the fuels. The sensor may further comprise a circuit for deriving the sensor voltage VSIG which compresses the range between the maximum and minimum possible values of sensor voltage VSIG relative to the range between the computer analog reference voltage ECM and the computer ground voltage EGD, with the output isolation amplifier providing a gain greater than one so as to provide a range between the maximum and minimum values of the fuel composition signal VOUT greater than the range between the maximum and minimum possible values of sensor voltage VSIG but still within the range between the computer analog reference voltage ECM and the computer ground voltage EGD.

The fuel composition sensor may provide the fuel composition signal VOUT having a maximum possible value substantially equal to the computer analog reference voltage ECM and a minimum possible value of the fuel composition signal a detectable fraction of a volt above the computer ground voltage EGD, so that a fuel composition signal VOUT equal to the computer ground voltage EGD indicates a sensor fault.

Further details and advantages of this invention will be apparent from the accompanying drawings and following description of a preferred embodiment.

SUMMARY OF THE DRAWINGS

FIGS. 2-4 are various views as indicated of a sensing capacitor for use in the fuel composition sensor according to the invention.

FIG. 6 shows a graph of dielectric constant vs. required air/fuel (A/F) ratio for combustion for a variety of fuels.

DESCRIPTION OF THE PREFERRED EMBODIMENT

Figure 1:
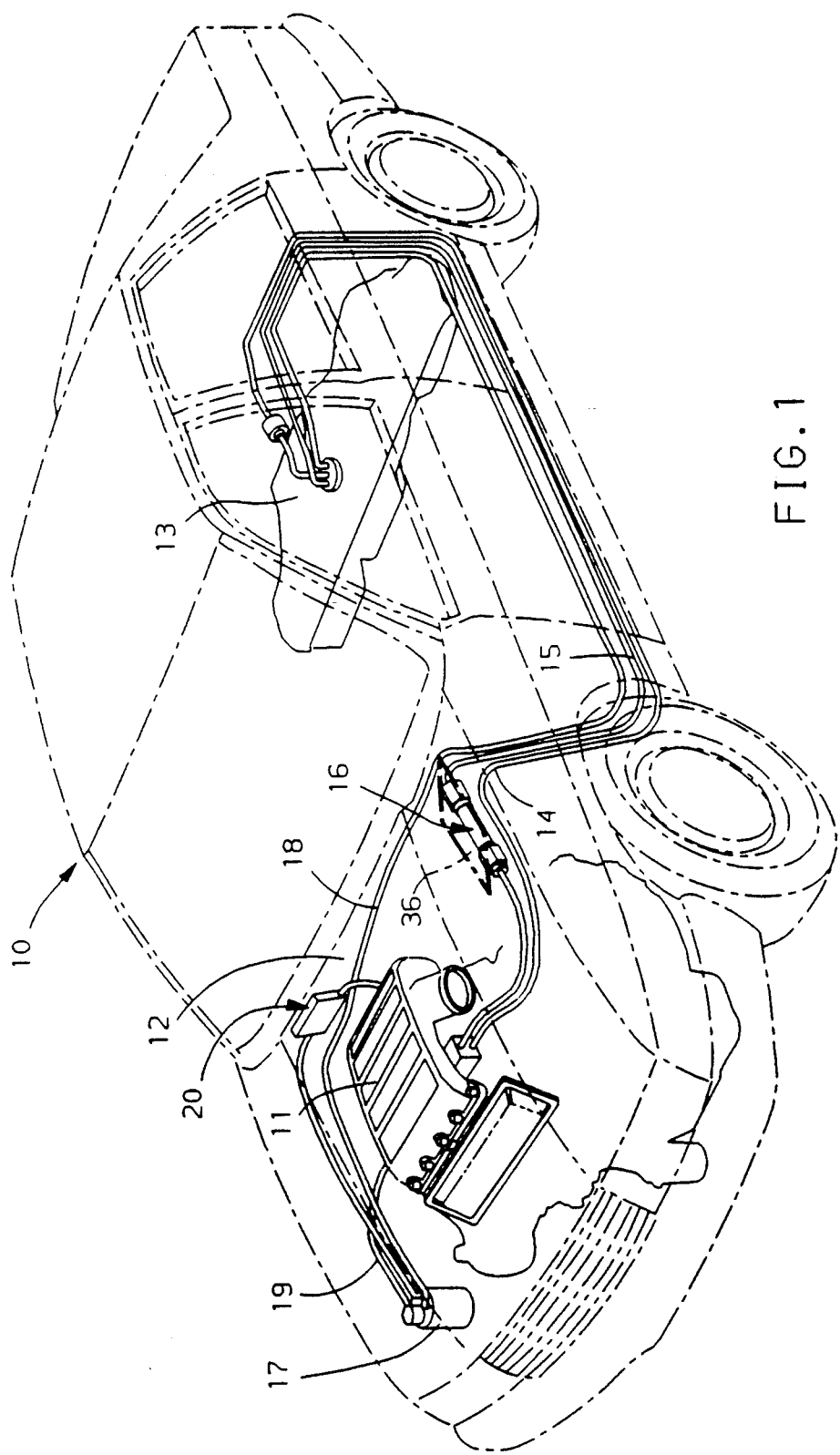
FIG. 1 shows a motor vehicle having an engine fuel control with a fuel composition sensor according to this invention.

Referring to FIG. 1, a motor vehicle 10 is provided with an internal combustion engine 11 in an engine compartment 12, engine 11 receiving fuel from a fuel tank 13 at the opposite end of the vehicle through a fuel conduit 15 and returning excess fuel to tank 13 through fuel conduit 14. The fuel in tank 13 is a mixture of essentially two fuels, one of which is gasoline and the other of which is an alcohol such as methanol or ethanol. Fuel conduit 15 includes a fuel composition sensor 16 located within engine compartment 12 at a point close to engine 11. Fuel composition sensor 16 generates a signal indicative of the relative proportion of alcohol to gasoline in the fuel flowing therethrough. A standard fuel vapor collection canister 17 is connected by a vapor conduit 18 to fuel tank 13 for collection of vapor therefrom and another vapor conduit 19 to the induction system of engine 11.

The operation of engine 11 is controlled by an electronic controller 20, which may be located at the rear of the engine compartment as shown or any other convenient location. Controller 20 may be a programmed digital computer similar to those presently used in motor vehicles for engine control. The apparatus is well known, comprising a microprocessor, RAM, ROM and appropriate input/output circuitry, with an appropriate program stored in ROM to coordinate receipt of input information from various sensors, perform calculations and table look-ups and output commands to various actuators of engine related components. Controller 20 is responsive to the fuel composition signal VOUT from fuel composition sensor 16 as well as a fuel temperature signal therefrom to modify such engine operating parameters as the air/fuel ratio, ignition timing, canister purge rate and/or others as necessary to optimize engine operation for the actual fuel mixture provided to the engine as sensed by sensor 16.

The mechanical structure of sensor 16 is shown in FIGS. 2-4. This structure provides for a common ground between the sensor case and the outer capacitor electrode, so that it is not necessary for these parts to be insulated from each other. The cost savings due to the grounded outer electrode are greater than the cost of any additional electronics required in the sensor due to this design feature.

An outer tube 26 of low carbon stainless steel has one end fitted within and laser welded to an extended open end of a coupling member 21 and another end fitted within and laser welded to an extended open end of another coupling member 22. Coupling members 21 and 22 are both made of stainless steel, have an outer hexagonal shape and define passages 23 and 24, respectively, therethrough, each of which passages 23 and 24 is provided with an internally threaded portion 27 and 2, respectively, for attachment in fuel line 15. Outer tube 26 forms a portion of the outer case of the sensor as well as the outer electrode of a sensor capacitor.

A stainless steel inner tube 40 is disposed axially within outer tube 26 to form the inner electrode of the sensor capacitor and to define an annular chamber 25 between tubes 26 and 40. Inner tube 40 is closed at each end in a tapered portion 41, a smaller diameter cylindrical portion 42 and an extended axial nipple 43, all made of stainless steel. Inner tube 40 is suspended at each end thereof within outer tube 26 by spacers 30, seen axially in FIG. 3. Each spacer 30 includes an inner portion 31 having a circular opening 32 which receives cylindrical portion 42 of inner tube 40 and three radially projecting legs 33 at 120 degree angles with respect to each other which end at outer tube 26, the legs 33 defining openings 34 therebetween. Spacers 30 may be made of an alcohol resistant, electrically insulating polymeric resin such as Nylon (R). A fuel flow path is thus defined through passage 24 of coupling member 22, through openings 34 between the legs 33 of a spacer 30, through annular chamber 25 between tubes 26 and 40, through openings 34 between the legs 33 of the other spacer 30, and through passage 23 of coupling member 21. The fuel in chamber 25 between tubes 26 and 40 forms the dielectric of the sensor capacitor defined by these electrodes.

A circuit board 36, of standard four layer (signal, power, ground, signal) construction, is attached to coupling member 21 by a machine screw 37, which not only physically anchors one end of board 36 but also provides a ground connection between a ground circuit trace on circuit board 36 and, through coupling member 21, tube 26, which thus comprises a grounded electrode of the sensor capacitor. Between screw 37 and the adjacent spacer 30, a glass insulator 38 is retained in an opening of coupling member 21 adjacent circuit board 36. A stainless steel pin 39 projects through circuit board 36 and insulator 38 so that it does not contact coupling member 21 or tube 26. Pin 39 is maintained in physical and electrical contact, as by welding or soldering, to the adjacent nipple 43 and is soldered on circuit board 36 to the appropriate circuit trace for the inner electrode of the sensor capacitor. The total distance between the connections of pin 39 to circuit board 36 and to nipple 43 is 9.7 mm. Thus, both the inner and outer electrodes of the sensor capacitor are electrically coupled to the circuit board through a minimal length of conductor.

The opposite end of circuit board 36 is attached by a pair of screws 44 to a clamp 45 comprising upper and lower clamp members 46, 47, respectively. Screws 44 hold clamp members 46 and 47 together as well as securing clamp 45 to circuit board 36. Clamp members 46 and 47 include matching semicircular openings which, together, define an inner circular opening 48 for receiving outer tube 26. Clamp 45 fits snugly around tube 26 to hold the opposite end of circuit board 36 in a stable manner without undue vibration relative to tube 26 but allows relative rotation so that twisting torques applied between coupling members 21 and 22 are not applied to circuit board 26. In practice, to protect the components of circuit board 36 and other parts of the sensor from the environment, a supplemental external case, not shown, may be attached to sensor 16 as by a machine screw in a threaded depression, not shown, opposite screw 37 and at clamp 45, for example by extending bolts 44 completely therethrough, to surround all of the sensor except the hexagonal ends of couplings 21 and 22.

A fuel temperature sensor 50 is received in a sealing manner in the wall of coupling member 22 so as to be exposed to fuel within and generate a fuel temperature signal communicated to an appropriate circuit trace(s) on circuit board 36 through wire leads 51 and 52. Fuel temperature sensor 50 may be a thermistor or any other type of temperature sensor appropriate for sensing the temperature of fluids and provides a necessary temperature correction signal for the sensor output. The fuel temperature signal may be separately output to engine control computer 20 for temperature compensation of the fuel composition signal VOUT.

Although all openings and gaps within the sensor are of sufficient size to prevent them from presenting a significant restriction to fuel flow, the total volume of fuel contained within chamber 25 is minimized with out of flow volumes eliminated or reduced to prevent extreme flow rate reduction or accumulation of fuel within chamber 25 which might lead to differences in dielectric constant between the fuel mixture in the sensor and that about to enter the combustion chamber of engine 11.

Figure 5:
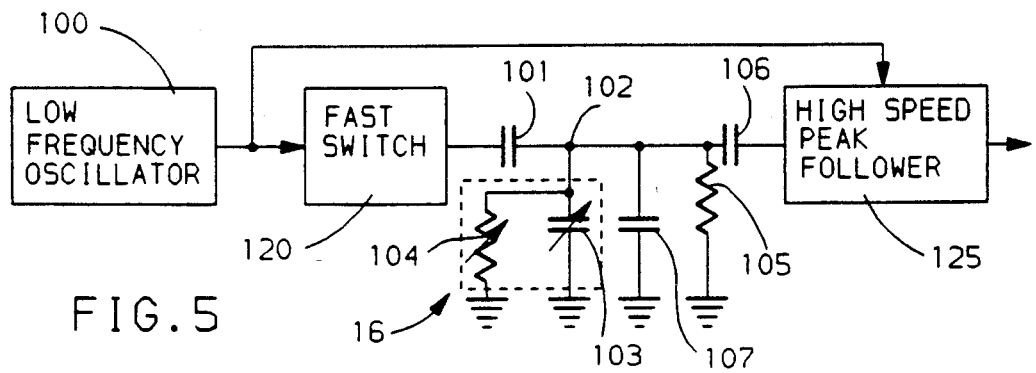
FIG. 5 shows a block and circuit diagram of a portion of a fuel composition sensor according to the invention.

The sensor electronics are shown in FIG. 5. These components are mounted on circuit board 36 in the sensor package. In an integrated circuit (IC) version of the circuit, as many of them as possible would be included in an IC that would be one of the circuit board components. The components are provided with a regulated voltage V+ of, for example, 6.5 volts and, through an input isolation amplifier to be described, a smaller regulated voltage VREF of 5.0 volts, both with reference to a sensor ground voltage terminal of the circuit board 36 and thereby tube 26 of the sensor capacitor defining a sensor ground voltage GND. The standard voltage regulator circuit for producing voltage V+ is not shown.

Referring to FIG. 5, a low frequency oscillator 100 generates an output voltage which varies between V+ and ground at a comparatively low frequency such as 6 KHz. This output voltage is adapted to control the conductive state of a fast switch 120, which alternately connects VREF and ground to one end of a reference capacitor 101 (680 pF) connected through sensor 16 to ground. Reference capacitor 101 and sensor 16 define a junction 102 therebetween so as to form a voltage divider with an output at junction 102. Sensor 16 comprises a sensor capacitor 103 having coaxial electrodes comprising tubes 26 and 40 of FIGS. 2–4 with a fuel mixture dielectric in chamber 25 therebetween as previously described and further comprises a parallel leakage resistance 104 through the fuel mixture in chamber 25. The capacitance of sensor capacitor 103 varies with the dielectric constant of the fuel mixture between its electrodes (e.g. 39–755 pF for gasoline and methanol); and leakage resistance 104 varies with the electrical conductivity of the same fuel mixture. Thus, each varies with fuel composition.

There will be a parasitic or stray capacitance of 6–10 pF from junction 102 to ground, but this does not affect the sensor output significantly and may, in any event, be taken into account in the circuit design. A bias resistor 105 (10K) is also provided between junction 102 and ground to provide a steady state ground bias at junction 102. A high speed peak detector 125 has a signal input connected through a DC blocking capacitor 106 (0.22 uF) to junction 102 and a latch input receiving the output of oscillator 100. A padding capacitor 107 (330 pF) provides improved linearity and gain resolution for more accurate response at high alcohol levels.

Figure 8:
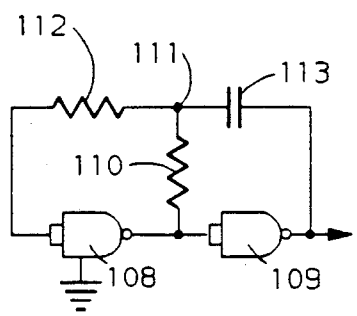
FIGS. 8-10 show diagrams of circuits for use as a low frequency oscillator, fast switch and high speed peak follower, respectively, in the fuel composition sensor of FIG. 5.

Low frequency oscillator 100 may be any convenient oscillator circuit capable of operating at a frequency at or near 6 KHz. An example is the relaxation oscillator of FIG. 8, utilizing series NAND gates 108 and 109 connected as series inverters. The output of inverter (NAND gate) 109 is connected back through a capacitor 113 (0.0047 uF) and resistor 110 (15K) in series to its input with the junction 111 of capacitor 113 and resistor 110 being connected through a resistor 112 (100K) to the input of inverter (NAND gate) 108 the output of which is connected to the input of inverter (NAND gate) 109. The component values are chosen to produce an oscillator output voltage which switches between the oscillator supply voltages (V+ and ground) at the desired 6 KHz frequency, as shown in waveform 180 of FIG. 7(A). This oscillator is a standard CMOS circuit well known to those skilled in the art and suitable for component assembly on a circuit board. In an IC version, this circuit would be replaced by another in the appropriate IC technology.

Figure 9:
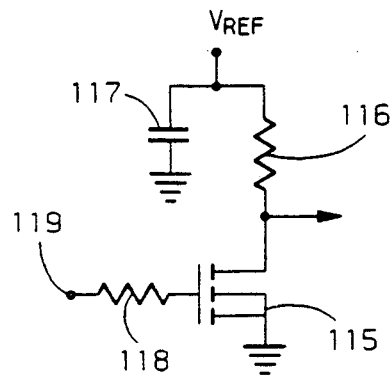

An example of fast switch 120 is shown in FIG. 9. A fast switching MOSFET 115, such as the Motorola (R) 2N7000 or its equivalent, is chosen to obtain a switching speed of 30 nanoseconds. Actually, the switching speed of the device with no added gate resistance is 10–15 nanoseconds; and a 510 ohm resistor 118 is placed in series with the gate to form a small RC delay with the internal gate capacitance and thus slow the switching speed down to the optimum 30 nanoseconds. MOSFET 115 has a grounded source and a drain connected through a resistor 116 (10K) to VREF, which is provided with a bypass capacitor 117 (0.22 uF) to ground to keep switching noise out of the power supply. The drain of MOSFET 115 is the output of fast switch 120, which output is connected to reference capacitor 101.

In operation, oscillator 100 causes MOSFET 115 to be turned on and off at a frequency of 6 KHz. The voltage at the drain of MOSFET 115 is shown in waveform 182 of FIG. 7(B) and approaches a 6 KHZ square wave. However, it is not a perfect square wave, since the voltage transitions are not instantaneous. The ramps of the voltage transitions are exaggerated for visibility in FIG. 7(B). Just before MOSFET 115 is turned on, the voltage on its drain is at VREF. Reference capacitor 101 is charged to VREF, with junction 102 at ground. As MOSFET 115 turns on, its drain voltage goes to ground in 30 nanoseconds. If there were no resistive current path to ground from junction 102, its voltage would drop, in the same time, to a voltage dependent on the capacitance ratio of reference capacitor 101 to sensor capacitor 103 and thus on the fuel composition. The 10K resistance of resistor 105 does not allow sufficient leakage current to significantly affect the fast voltage drop at junction 102; however, it allows the capacitors to discharge after the immediate voltage drop so that the voltage on junction 102 returns to ground.

However, leakage resistance 104 will be much smaller than the 10K of resistor 105 at high methanol concentrations (above 30 percent methanol, for example) and will allow a significant portion of the capacitor charge to leak away before MOSFET 115 turns completely on unless the switching of fast switch 120 is extremely fast. Such a loss of charge would result in the voltage at junction 102 not dropping as far before rising again; and the abbreviated voltage peak would create an error in the indicated fuel composition. The faster the switching of fast switch 120, up to a point, the less charge will be lost and the more accurate will be the downward voltage spike at junction 102 in indicating the fuel composition. A single bipolar transistor, with a typical switching time of 70–100 nanoseconds, is not fast enough. A network of bipolar transistors can be constructed with a faster switching time, at the price of additional cost and circuit complexity. MOSFET 115, as previously mentioned, has a switching time (in turning on) of 10–15 nanoseconds; but this is too fast, due to the inductance of the leads (pin 48 and the combination of coupling 21 and screw 37) of sensor capacitor 103 between electrode members 26 and 40 and the circuit board. This inductance causes inaccuracies at very fast switching speeds. For example, the inductance can produce a ringing which causes a delay in the downward voltage spike at junction 102 while energy is temporarily stored in the inductive fields of the leads. More charge can leak off the capacitors during this ringing. Also, the inductance of the leads produces a voltage drop along the leads of about 50 millivolts for each ¼ inch of lead—at each end of the capacitor. Each of these factors contributes to the inaccuracy of the sensor; and this inaccuracy tends to increase with the speed of switching. It has been determined that a 30 nanosecond switching time provides the optimum signal with the lowest error at high methanol concentrations. Lower switching speeds allow more charge to leak off for a more abbreviated output voltage peak. However, faster switching speeds increase error due to the inherent inductances of the sensor capacitor leads.

There are additional considerations of importance in the design of the circuit described to this point. Resistor 116 is given a value of 10K. This value is chosen as a compromise between competing factors. It is desired that, when MOSFET 115 is on or conducting, the voltage at its drain be essentially ground. Actually, its drain voltage will be determined by the voltage divider effect of resistor 116 over the internal drain/source impedance of MOSFET 115, which is a few ohms. The larger the resistance of resistor 116, the closer the drain voltage will be to ground during MOSFET conduction. However, it is also necessary that reference capacitor 101 be recharged to a full VREF during each oscillator cycle prior to the turning on of MOSFET 115. Since resistor 116 is in the charging path of reference capacitor 101, an increase in its resistance means a longer charging time; and 20K produces too long a time for the other component values used. The oscillator frequency is likewise a compromise between competing factors. A lower frequency will increase the size of an integrating capacitor 150, yet to be described; and this will slow the overall sensor response time. However, a higher frequency would allow even less time for the recharging of reference capacitor 101 during each oscillator cycle and put additional downward pressure on the resistance of resistor 116 as described above.

Figure 7:
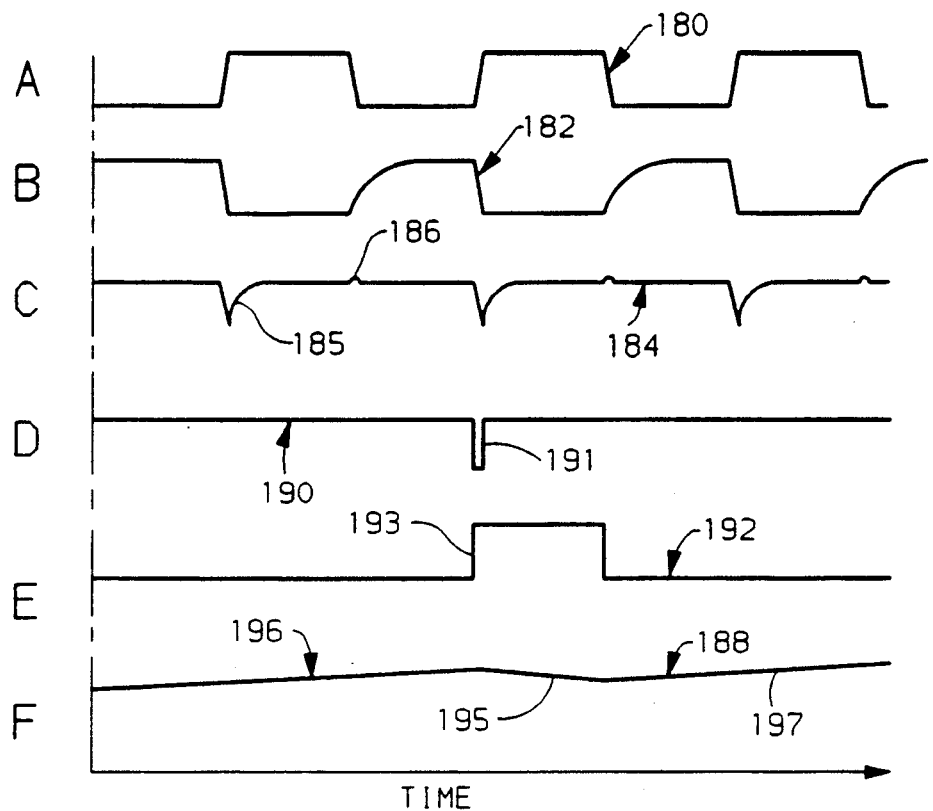
FIG. 7 shows a series of voltage waveforms useful in understanding the operation of the circuit of FIG. 5.

The voltage waveform 184 at junction 102 is seen in FIG. 7(C). Each downward spike 185 is a new capacitance (and therefore fuel composition) measurement. The smaller upward spikes 186 are due to the same effect in the opposite direction during the alternate oscillator phases as MOSFET 115 is turned off. These upward spikes are ignored in the following circuitry. The voltage at junction 102 is upward shifted and peak detected by the following high speed peak detector 125 to provide an analog output signal between ground and VREF.

Figure 10:
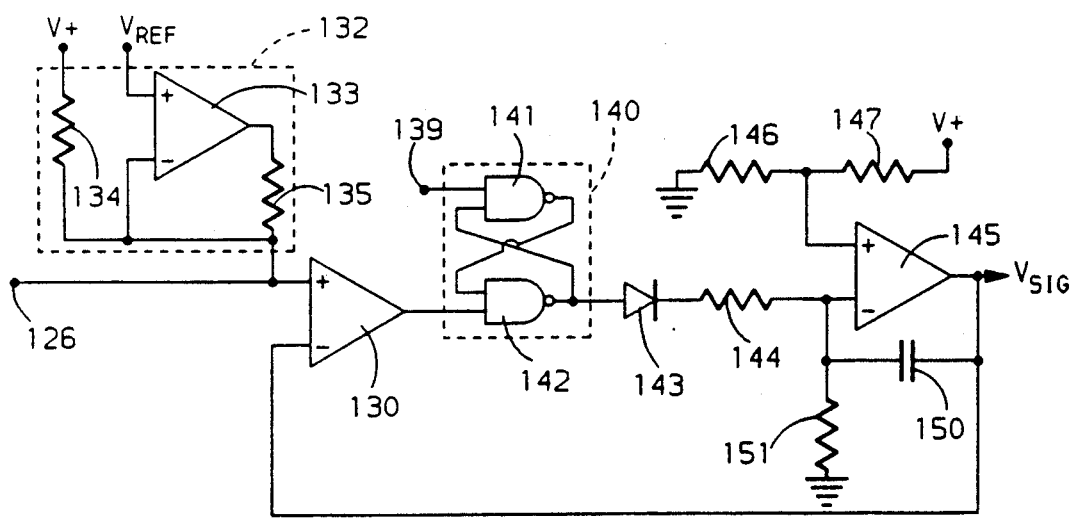

An embodiment of high speed peak detector 125 is shown in FIG. 10. Input terminal 126 from capacitor 106 is connected to a pull-up circuit 132 which comprises an op-amp 133 (LM158) having a non-inverting input connected to VREF, an inverting input connected through a resistor 134 to V+ and an output connected through a resistor 135 (10K) to terminal 126 and to its inverting input. This circuit shifts the voltage at junction 102 upward by VREF to get it above ground for the following circuitry, with DC blocking capacitor 106 of FIG. 5 separating the different voltage level portions of the circuit.

Terminal 126 is also connected to the non-inverting input of a fast comparator 130 (LT1016), the inverting output of which is provided to one input of a NAND gate latch 140 having another input 139 connected to the output of low frequency oscillator 100. The output of latch 140 is provided through a diode 143 and resistor 144 (100K) to the inverting input of an op-amp 145 (LM158) having a non-inverting input provided with a constant reference voltage from a voltage divider comprising resistors 146 and 147 in series across voltage V+. The output of op-amp 145 is fed back to the inverting input through a capacitor 150 (0.33 uF) and is further provided as the output of the sensor and as a reference to the inverting input of fast comparator 130. The inverting input of op-amp 145 is connected through a resistor 151 (750K) to ground. Fast comparator 130 requires a higher DC bias current than normal slower comparators, which is provided by circuit 132. Circuit 132 has a high impedance during the downward spikes 185 of FIG. 7(C) so as to reduce sensor inaccuracy due to this high DC bias current.

The operation of the remainder of the circuit of FIG. 10 will be described with relation to the waveforms of FIGS. 7(D)–7(F). Sensor voltage VSIG, determined by an integrator comprising op-amp 145 and its feedback capacitor 150, is shown as waveform 188 of FIG. 7(F). During each half oscillator cycle in which the oscillator output is low, the latch output of NAND gate 142 is held low and capacitor 150 is allowed to discharge through resistor 151. The comparatively high value of resistor 151 assures a slow discharge for a slowly rising VSIG. During the opposite half cycle of oscillator 100, in which the oscillator output is high, the latch output remains low unless the high speed comparator output goes low, which will occur if the downward spike of the voltage at junction 102, shifted upward by circuit 132, falls below the sensor voltage VSIG. The output of fast comparator 130 is shown as waveform 190 of FIG. 7(D); and one such downward spike 191 is shown. The response of latch 140 is to switch its output, shown as waveform 192 of FIG. 7(E), high for the remainder of the oscillator half cycle, as shown at 193. Capacitor 150 will charge through diode 143 and resistor 144, at a significantly faster rate than the discharge due to the smaller value of resistor 144; and sensor voltage VSIG will thus fall comparatively rapidly, as shown in portion 195 of waveform 188. The usual constant slow rise of VSIG, as shown in portions 196 and 197 of waveform 188, is punctuated by briefer, faster falls, as shown in portion 195, as VSIG follows the downward peaks of the voltage at junction 102 to maintain a level indicating the capacitance of sensor capacitor 103 and therefore of fuel composition.

Figure 11:
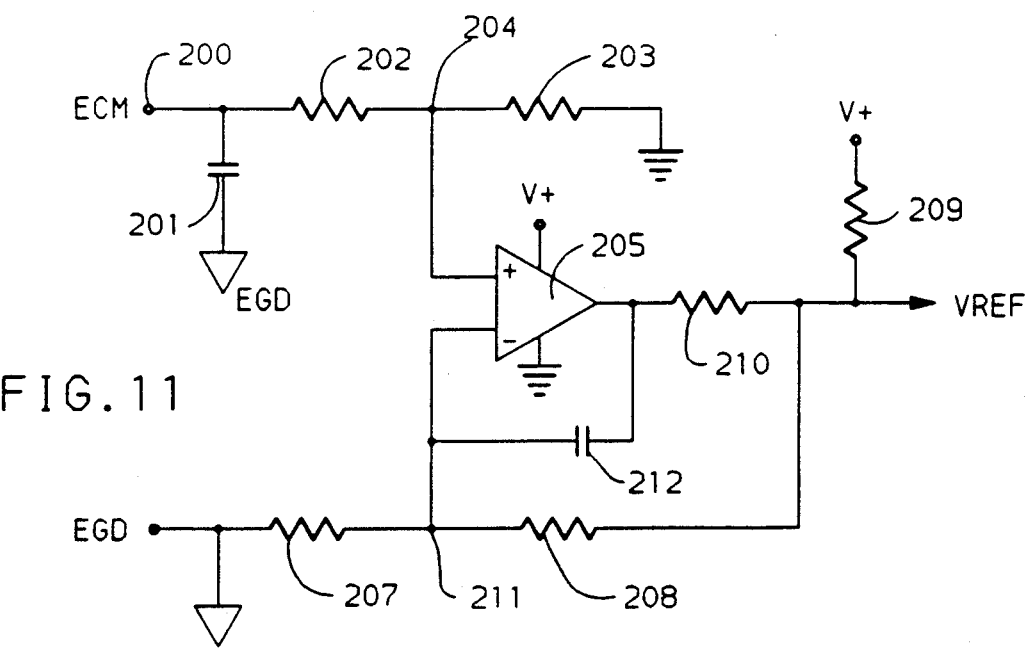
FIGS. 11 and 12 show circuit diagrams of input and output isolation amplifiers, respectively, comprising additional portions of a fuel composition sensor according to the invention.

FIG. 11 shows the input isolation amplifier, also located on circuit board 36. A computer analog reference voltage ECM of engine control computer 20 is nominally 5.0 volts with reference to the engine control computer ground EGD, which ground may vary up to a volt with respect to the sensor ground GND. The input isolation amplifier generates an output differential voltage VREF-GND which is ratiometric with the input voltage difference ECM-EGD. FIG. 11 shows an input terminal 200 receiving voltage ECM and connected through a capacitor 201 (0.001 uF) to computer ground EGD and through series resistors 202 (10.0K) and 203 (10.0K) to sensor ground GND. In these Figures, sensor ground GND is shown with a standard parallel line ground symbol and computer ground EGD is shown with an inverted triangle symbol. Junction 204 of resistors 202 and 203 is connected to the non-inverting input of an op-amp 205 (LM124). Computer ground EGD is connected through series resistors 207 (10.0K) and 208 (10.0K) to an output terminal VREF, which is connected through a resistor 209 to voltage V+ and through a resistor 210 (36 ohm) to the output of op-amp 205. Junction 211 of resistors 207 and 208 is connected to the inverting input of op-amp 205 and through a capacitor 212 (0.001 uF) to the output of op-amp 205.

Op-amp 205, with resistors 202, 203, 207 and 208 comprises a standard ratiometric voltage shifting circuit in which a differential output voltage is equal to a gain factor times the differential input. Capacitor 212 and resistor 210 are provided because the output is intended to drive a capacitive load. Since op-amp 205 is referenced to sensor ground GND, the differential output is VREF-GND, whereas the differential input is ECM-EGD. The gain factor in this case (determined by the resistance ratio of resistors 203 and 202 or the identical resistance ratio of resistors 208 and 207) is unity, since all the gain determining resistors are identical. The equivalent equation for the circuit of FIG. 11 is thus:

$$VREF - GND = ECM - EGD.$$

The differential output voltage VREF-GND of the circuit of FIG. 11 is applied across resistor 116 and switching MOSFET 115 of FIG. 9 in the sensor circuit of FIG. 5, so that the voltage applied to the sensor capacitor is thus ratiometric with the analog reference voltage of computer 20, although it is referenced to sensor ground. VREF is also provided to the pull-up circuit 132 described with reference to FIG. 10. The equivalent equation for the sensor circuit of FIGS. 5, 8, 9 and 10 is $$VSIG - GND = (VREF - GND)(1 - CAPRATIO).$$

wherein CAPRATIO is the capacitance ratio $C_{101}/(C_{101}+C_{103}+C_{107}+C_{stray})$, wherein $C_{101}$, $C_{103}$ and $C_{107}$ are the capacitances of reference capacitor 101, sensor capacitor 103 and padding capacitor 107, respectively and $C_{stray}$ is the stray capacitance of the sensor. Sensor voltage VSIG of the circuit of FIG. 10, which indicates the fuel composition signal, is somewhat compressed with respect to the full analog reference voltage: having a voltage range over the full fuel composition range of about 1.25 volts (1.75 to 3.0 volts). An output isolation amplifier is provided to expand the output range as closely as possible to the full five volts of ECM-EGD and to reference this voltage to computer ground EGD.

Figure 12:
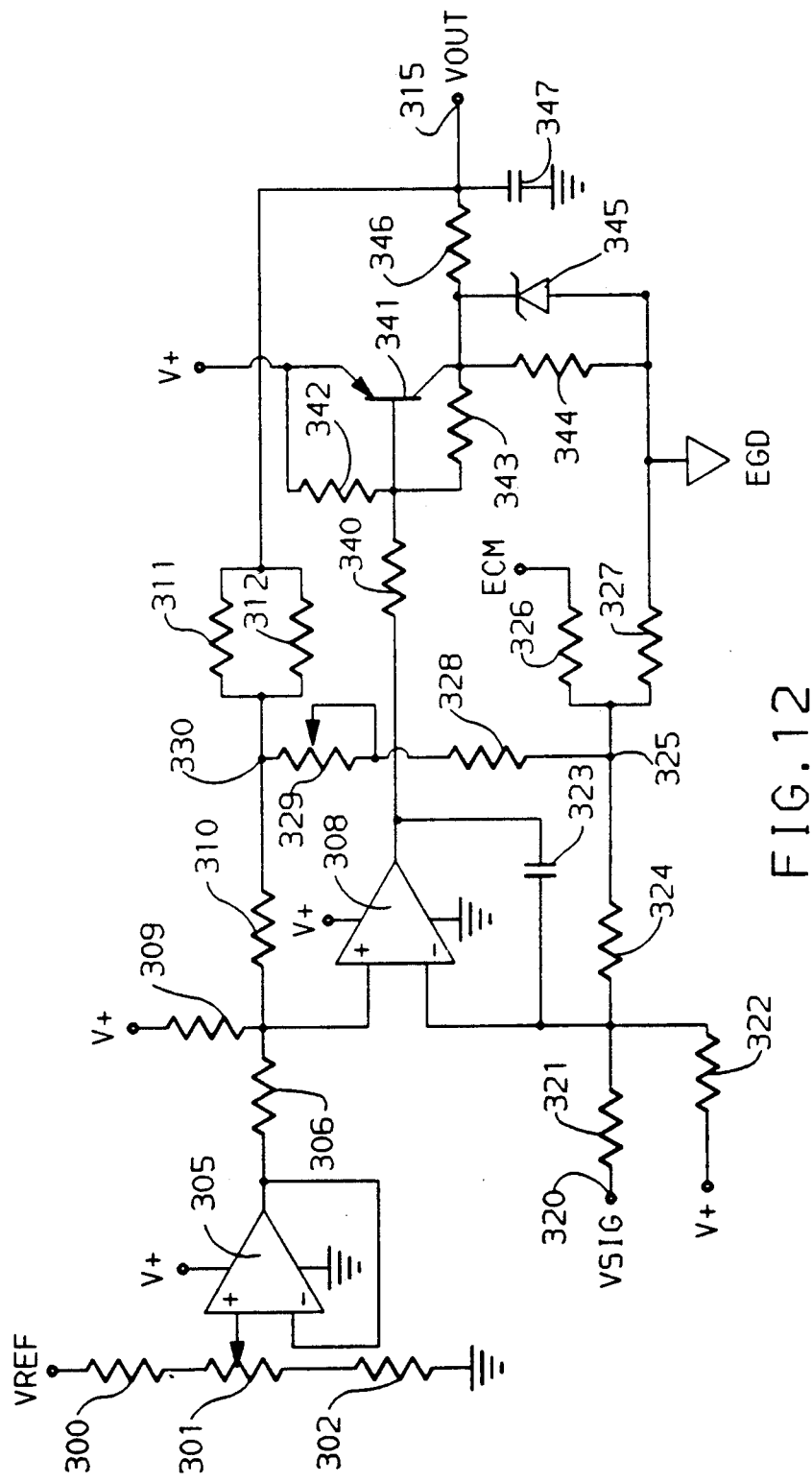

FIG. 12 shows the output isolation amplifier, the output voltage VOUT of which is the fuel composition signal provided to engine control computer 20. Voltage VREF is connected to the top of a voltage divider comprising resistor 300 (2.7K) a variable tapped resistor 301 (1K series) and resistor 302 (510 ohm) in series, the bottom of the voltage divider (resistor 302) being connected to sensor ground GND. The variable tap of resistor 301 is connected to the non-inverting input of an op-amp 305 (LM124), the output of which is connected to the inverting input to form a unity gain buffer amplifier and is also connected through a resistor 306 (20.0K) to the non-inverting input of an op-amp 308 (LM124). The non-inverting input of op-amp 308 is further connected through a resistor 309 (100.0K) to voltage V+ and through a resistor 310 (10.0K) in series with the parallel combination of resistors 311 (90.0K) and 312 (10.0K) to an output terminal 315. The variable tap of resistor 301 is adjusted to provide a voltage to the non-inverting input of op-amp 308 equal to VSIG with a fuel mixture of pure gasoline (no alcohol).

Voltage VSIG is provided to an input terminal 320, which is connected through resistor 321 to the inverting input of op-amp 308. The inverting input of op-amp 308 is further connected through a resistor 322 (100.0K) to voltage V+, through a capacitor 323 to the output of op-amp 308, and through a resistor 324 (10.0K) to the junction 325 of a pair of series resistors 326 (90.0K) and 327 (10.0K) forming a voltage divider across the differential voltage ECM-EGD. Junction 325 is further connected through a resistor 328 (10.2K) and a variable resistor 329 in series to the junction 330 of resistors 310, 311 and 312.

The output of op-amp 308 is connected through a resistor 340 (15K) to the base of a bipolar PNP transistor 341 having an emitter connected to voltage V+ and also through a bias resistor 342 (5.1K) to its base. Transistor 341 has a collector connected through a bias resistor 343 (30K) to its base and through a resistor 344 to computer ground EGD. The collector of transistor 341 is also connected through a zener diode 345 (5.6 volts) to EGD and through a resistor 346 to output terminal 315, which output terminal is connected through a capacitor 347 (0.001 uF) to ground and upon which appears the fuel composition signal VOUT.

The output isolation amplifier of FIG. 12 is built upon the same basic op-amp circuit as is shown in FIG. 11; but with some additional complications. The basic circuit comprises op-amp 308 with one input connected to a voltage divider between two voltages and the other input connected to a voltage divider between a voltage and the output (through negative feedback). In the circuit of FIG. 12, the input voltages are VSIG through resistor 321, VSIG for pure gasoline (minimum VSIG, about 1.75 volts) through resistor 306, and 0.1 (ECM-EGD) through a combination of resistors 326, 327, 324, 328 and 329. The negative feedback path is through a combination of resistors 311, 312, 310, 328 and 329. Resistors 306 and 321 are identical, as are resistors 310 and 324. The parallel combination of resistors 311 and 312 is identical with the parallel combination of resistors 326 and 327. Resistors 328 and 329 are common to both combinations, with resistor 329 allowing common simultaneous adjustment of the gain ratio on both the inverting and non-inverting sides of the circuit. This gain is greater than unity so as to expand the output range as previously discussed. The feedback is negative but is provided to the non-inverting input due to the output signal inversion by transistor 341. The connections to voltage V+ through resistors 309 and 322 raise the input common mode voltage.

As already mentioned, the output isolation amplifier of FIG. 12 expands the fuel composition dependent compressed range of VSIG. In particular, the expansion provides for a minimum of 0.5 volts, as determined by the voltage divider of resistors 326 and 327 across ECM-EGD and a maximum of 5 volts. One benefit of using a 0.5 volt minimum is that a zero volt output, relative to EGD, cannot be obtained in normal operation of the sensor. Such an output thus indicates a sensor fault and may be used for diagnostic purposes.

Op-amp 308 typically has a maximum output voltage range of about 1.5 volts below the upper supply voltage to a few tenths of a volt above the lower supply voltage. Since it is supplied between V+ and sensor GND, this would appear to be sufficient for a voltage range of 0.5 to 5.0 volts. However, since the output of the circuit is relative to computer ground EGD, which can vary up to a volt from sensor ground GND, a wider possible voltage range may be required. The output stage comprising transistor 341 has an output which is capable of ranging up to a diode drop below V+ (5.9 volts) relative to GND and down to within a few tenths of a volt above computer ground EGD. In the worst case wherein EGD is a full volt below GND, this provides the 6.5 volt range required. A smaller range will be provided as EGD increases relative to GND; however, the required range will decrease by the same amount. Thus the circuit provides the wider range as required.

The equivalent equation of the output isolation amplifier is $$VOUT - EGD = K(VSIG - VSIG_{min}) + 0.1(ECM - EGD).$$

wherein $VSIG_{min}$ is the minimum value of VSIG (for sensed pure gasoline) and K is a gain constant determined as previously described. Since this output is with reference to computer ground EGD, EGD = 0. Since K is adjusted so that VOUT = ECM − EGD when VSIG is at its maximum value ($VSIG_{max}$), the equation may be expressed as $$VOUT = K(VSIG - VSIG_{min}) + 0.1(ECM).$$

wherein $K = 0.9(ECM)/(VSIG_{max} - VSIG_{min})$. For the values described above, the equation is approximately $$VOUT = 3.5(VSIG - 1.75) + 0.5.$$

VSIG is ratiometric with ECM-EGD and ranges over all but the lowest 0.5 volts of the total allowed input to the engine control computer for maximum resolution and accuracy. Output voltage VOUT of the output isolation amplifier of FIG. 12 is the fuel composition signal provided to an input of engine control computer 20. It is referenced to computer ground EGD and has a maximum allowable range less than but close to the input range ECM − EGD = 5.0 volts to use as much of the allowable input range as possible for the greatest resolution in the analog to digital converters of computer 20.

The embodiments of the invention in which an exclusive property or privilege is claimed are defined as follows:

1. A fuel composition sensor for a fuel mixture in a fuel supply line for a combustion engine wherein the fuel mixture comprises two fuels of different dielectric constants in unknown relative concentrations, one of the fuels being electrically conductive, the combustion engine having a control computer comprising an electric power supply defining a computer analog reference voltage ECM referenced to a computer ground voltage EGD and an input adapted to receive a fuel composition signal VOUT from the sensor varying in a range between the computer analog reference voltage ECM and the computer ground voltage EGD, the sensor comprising, in combination:

a capacitive sensor in the fuel line provided with a sensor analog reference voltage VREF referenced to a sensor ground voltage GND, which sensor ground voltage GND may differ from the computer ground voltage EGD, for providing a fuel composition responsive sensor voltage VSIG referenced to the sensor ground voltage GND, the sensor voltage VSIG having a minimum possible value $VSIG_{min}$ corresponding to a sensed fuel composition of only one of the fuels;

an input isolation amplifier generating the sensor analog reference voltage VREF referenced to the sensor ground voltage GND ratiometrically from the computer analog reference voltage ECM referenced to the computer ground voltage EGD; and an output isolation amplifier generating the fuel composition signal VOUT relative to the computer ground voltage EGD, less a constant, ratiometrically from the difference between the sensor voltage VSIG and the minimum possible value of the sensor voltage $VSIG_{min}$.

2. The fuel composition sensor of claim 1 in which the capacitive sensor comprises a voltage divider comprising a sensor capacitor in series with a reference capacitor for determining a proportion of the sensor analog reference voltage VREF relative to the sensor ground voltage GND indicative of fuel composition for derivation of the sensor voltage VSIG.

3. The fuel composition sensor of claim 2 in which the sensor signal VSIG has a maximum possible value $VSIG_{max}$ corresponding to a sensed fuel composition of only the other of the fuels, the difference $VSIG_{max} - VSIG$ is less than the difference ECM − EGD, and the output isolation amplifier provides a gain greater than one so as to provide a range between the maximum and minimum values of the fuel composition signal VOUT greater than the difference $VSIG_{max} - VSIG_{min}$ but not greater than the difference ECM − EGD.

4. The fuel composition sensor of claim 3 in which the maximum possible value of the fuel composition signal VOUT is substantially equal to the computer analog reference voltage ECM and the minimum possible value of the fuel composition signal VOUT is a detectable fraction of a volt above the computer ground voltage EGD, whereby a fuel composition signal VOUT equal to the computer ground voltage EGD indicates a sensor fault.

5. A fuel composition sensor according to claim 1 in which the fuel is a mixture of gasoline and alcohol and the minimum possible value of the sensor voltage $VSIG_{min}$ corresponds to a mixture of pure gallons.

6. A fuel composition sensor according to claim 1 in which the sensor analog reference voltage VREF referenced to the sensor ground voltage GND and generated by the input isolation amplifier is equal in magnitude to the computer analog reference voltage ECM referenced to the computer ground voltage EGD.

7. A fuel composition sensor according to claim 1 in which the input isolation amplifier comprises an operational amplifier referenced to the sensor voltage ground GND and having an output providing the sensor analog voltage VREF, one input connected through a first resistor to the output of the operational amplifier and a second resistor to the computer ground voltage EGD and another input connected through a third resistor to the sensor voltage ground GND and a fourth resistor to the computer analog reference voltage ECM.

8. A fuel composition sensor according to claim 7 in which the first, second, third and fourth resistors all have equal resistances.

9. A fuel composition sensor according to claim 1 in which the output isolation amplifier comprises an operational amplifier referenced to the sensor voltage ground GND and having an output providing the output voltage VOUT, one input connected through a first resistor to the sensor voltage VSIG and a second resistor to the computer ground voltage EGD and another input connected through a third resistor to the output of the operational amplifier and a fourth resistor to a predetermined voltage referenced to the sensor ground GND.

10. A fuel composition sensor according to claim 9 in which the fuel is a mixture of gasoline and alcohol and the predetermined voltage is the value of VSIG for a mixture of pure gasoline.

* * * * *